United States Patent [19]
Charpak

[11] Patent Number: 5,959,302
[45] Date of Patent: Sep. 28, 1999

[54] HIGH RESOLUTION RADIOGRAPHIC IMAGING DEVICE

[76] Inventor: Georges Charpak, 2 Rue de Poissy, Paris, France, 75005

[21] Appl. No.: 08/863,527

[22] Filed: May 27, 1997

[30] Foreign Application Priority Data

May 29, 1996 [FR] France .................................. 96 06600

[51] Int. Cl.⁶ .................................................. G01T 1/185
[52] U.S. Cl. ...................... 250/385.1; 250/374; 250/583; 378/37; 378/146; 378/98; 382/132
[58] Field of Search ................................ 250/385.1, 374, 250/583; 378/37, 146, 98; 382/132

[56] References Cited

U.S. PATENT DOCUMENTS

| | | |
|---|---|---|
| 5,032,729 | 7/1991 | Charpak . |
| 5,308,987 | 5/1994 | Wuest et al. . |
| 5,347,131 | 9/1994 | Charpak ................................ 250/385.1 |
| 5,374,131 | 12/1994 | Ito et al. . |
| 5,521,956 | 5/1996 | Charpak . |

FOREIGN PATENT DOCUMENTS

2190787  11/1987  United Kingdom .

*Primary Examiner*—Constantine Hannaher
*Assistant Examiner*—Andrew Israel
*Attorney, Agent, or Firm*—Larson & Taylor

[57] ABSTRACT

A high resolution radiographic imaging device for medical or industrial radiography includes at least one ionizing particles detector equipped with at least one gas chamber provided with a window for the lateral or frontal inlet of the illumination beam. A first, a second and a third flat electrode are placed in parallel with one another in order to form a conversion space and a amplification space with the distance separating the second and third electrodes being less than 200 μm and the amplitude ratio of the electrical fields created between the second and third electrodes and the first and second electrodes being greater than 10.

15 Claims, 8 Drawing Sheets

HIGH RESOLUTION RADIOGRAPHIC IMAGING DEVICE

The invention relates to a high resolution radiographic imaging device.

In general, the present radiographic imaging devices are subject to two essential constraints: increasing the resolution of the images obtained and reduction of the radiation doses applied to the subject to be observed, in particular by reduction of the time of exposure of the latter to the ionizing radiation.

With regard to increasing the resolution of the images, such an objective appears, above all, to be related to the fineness of detection of the ionizing radiation illuminating the observed subject, to the spatial fineness of the physical patterns generated by this detection process and, finally, to the geometric fineness of the detector elements allowing these physical patterns to be revealed.

Furthermore, the use of very high resolution detector elements, and therefore of very small size and having a high amplification gain, is susceptible to allow an appropriate distribution of a plurality of this type of detector element over a specific observation field and consequently a reduction in the illumination time necessary for the observation of this field to that necessary for the observation of an elementary field corresponding to that of one detector element, which consequently makes it possible to reduce significantly the radiation doses applied to the subject to be observed.

A purpose of the present invention is the use of a high resolution radiographic imaging device making it possible to satisfy the constraints mentioned above.

Another purpose of the present invention is the use of a radiographic imaging device in which the image resolution is better than 100 µm.

Another purpose of the present invention is the use of a radiographic imaging device in which the time of exposure of a subject can be reduced by a factor of 10 with respect to the devices of the prior art.

The high resolution radiographic imaging device using ionizing radiation which is the subject of the present invention comprises a source of ionizing radiation in the form of a divergent beam, a longitudinal slot forming a diaphragm making it possible to deliver a flat illumination beam, substantially distributed in a plane containing the longitudinal slot, and a module for detecting a beam transmitted through a subject to be observed, illuminated by the flat illumination beam.

It is noteworthy in that the detector module comprises at least one ionizing particles detector comprising at least one gas chamber provided with an inlet window for the illumination beam. The gas chamber comprises a first, a second and a third flat electrode, each flat electrode being placed parallel with one another in order to form a space for the conversion of the illumination beam into electrons and a space for the amplification of these electrons. The inlet window is placed at the level of the conversion space in order to ensure the inlet of the illumination beam into the conversion space and the amplification space has a multiplication length, the distance separating the second and the third electrodes, of less than 200 µm. The detector furthermore comprises a biasing circuit making it possible to raise the first electrode to a first electrical potential, the second electrode to a second electrical potential higher than the first electrical potential, and the third electrode to a third electrical potential higher than the second electrical potential. The second electrode pierced with holes forms a cathode allowing the transmission of the electrons generated in the conversion space towards the amplification space, and the third electrode forms an anode constituted by a plurality of electrically isolated elementary anodes. The electrical potentials applied to the first, to the second and to the third electrodes allow the generation of a first and a substantially parallel second electrical field in the conversion space and in the amplification space, each of these fields being substantially perpendicular to the electrodes with an amplitude ratio greater than 10 in order to ensure the multiplication of these electrons in the amplification space by an avalanche phenomenon, confined to the amplification length, and to generate multiplied electrons in the vicinity of the third electrode forming an anode. Circuits for detecting and counting the multiplied electrons are coupled to the elementary anodes forming the anode.

The high resolution radiographic imaging device is applicable both to industrial radiographic imaging, in particular in the fields of crystallography and strength of materials, and to medical radiographic imaging.

It will be better understood on reading the following description and on observing the drawings in which.

A more detailed description of a high resolution radiographic imaging device using ionizing radiation, according to the subject of the present invention, will now be given with reference to FIGS. 1a and 1b.

Figure 1A:
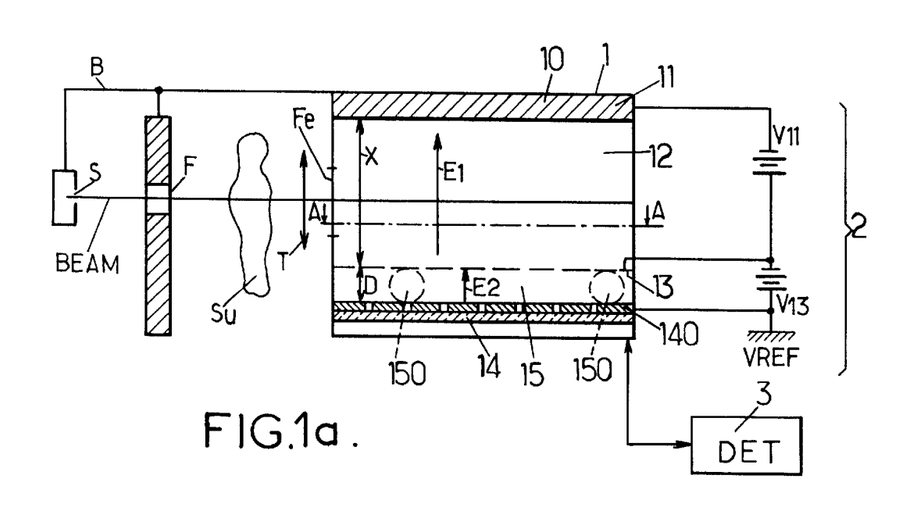
FIGS. 1a and 1b show a longitudinal cross-sectional view of a high resolution radiographic imaging device which is the subject of the present invention.

The said FIG. 1a is a cross-sectional view along a plane of longitudinal symmetry of this device, this plane of longitudinal symmetry being, by definition, the plane of the paper on which FIG. 1a is shown.

As can be observed in the said figure, the device according to the invention comprises an ionizing radiation source, referenced S, delivering ionizing radiation in the form of a divergent beam, and a longitudinal slot, referenced F, forming a diaphragm, allowing the delivery of an illumination beam. In a conventional way, this illumination beam is a flat beam of X or γ (gamma) rays substantially distributed in the plane containing the longitudinal slot F, that is to say in a plane perpendicular to the plane of the paper on which FIG. 1a is shown. The said illumination beam makes it possible to illuminate a subject SU to be observed, this illumination beam, after selective absorption according to the density zones of the subject to be observed SU, being received by a detection module, referenced 1 in the said FIG. 1a.

According to a particularly advantageous aspect of the device which is the subject of the present invention, it is pointed out that the detection module 1 comprises at least one ionizing particles detector comprising a gas chamber 10, provided with a window for the inlet of the illumination beam.

The gas chamber 10 is a chamber of the conventional type having a window for the inlet of the flat illumination beam, the window being referenced Fe, and elements for the inlet of a filling gas, these inlet elements not being shown in the drawings in order not to complicate the latter. The gas let into the gas chamber can, in a conventional way, be inlet under a slight excess pressure with respect to atmospheric pressure or, on the contrary, either at a relatively high pressure, or at a very low pressure, close to a few Torr, depending on the operating conditions of the radiographic imaging device which is the subject of the invention.

Figure 1B:
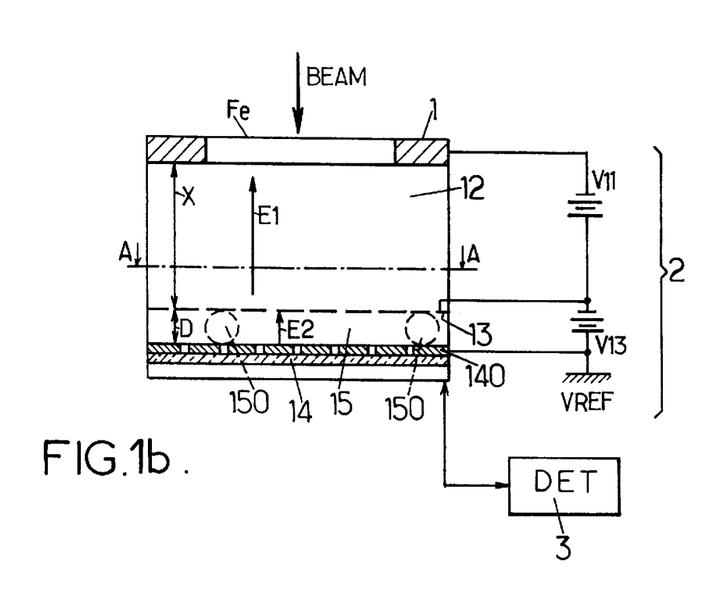

As furthermore seen in FIGS. 1a and 1b, the gas chamber 10 comprises a first electrode, referenced 11, a second electrode, referenced 13, and a third electrode, referenced 14, these electrodes being flat and placed parallel with one another in order to form a conversion space, referenced 12, for converting the illumination beam into electrons, and a space for amplification by multiplication of these electrons, this amplification space being referenced 15.

The inlet window Fe is placed at the level of the conversion space 12 and makes it possible to ensure the inlet of the illumination beam into the conversion space 12 parallel with the first electrode, 11, and with the second electrode, 13, in the case of the embodiment shown in FIG. 1a.

In the embodiment shown in FIG. 1a, the inlet window Fe is thus placed laterally on the gas chamber 10 in order to allow the inlet of the illumination beam parallel with the cathode 13 and anode 14 electrodes.

On the contrary, in the embodiment shown in FIG. 1b, the inlet window Fe is placed on the face of the gas chamber located opposite the second cathode electrode 13 in order to allow a frontal inlet of the illumination beam with respect to the electrodes.

It is of course understood that the assembly constituted by the source S, the slot F materialized by a diaphragm made of lead for example, and the detector module 1 can be rendered integral by means of a frame B, this assembly being able to be manoeuvred in translation and, if necessary, in rotation, in order to ensure an appropriate analysis of the subject SU. The mechanical embodiment of the assembly will not be described in detail because the elements necessary for this embodiment are known to those skilled in the art. Furthermore, the source S and the detector module 1 can be fixed, the subject SU being moved with an appropriate displacement.

According to a particularly advantageous characteristic of the device which is the subject of the present invention, it is pointed out that the amplification space 15 has a multiplication length, that is to say a distance D separating the second electrode, 13, and the third electrode, 14, of less than 200 μm.

According to another particularly noteworthy characteristic of the device which is the subject of the present invention, it is pointed out that the latter comprises a biasing circuit, referenced 2, making it possible to raise the first electrode 11 to a first electrical potential, the second electrode 13 to a second electrical potential higher than the first one, and the third electrode 14 to a third electrical potential higher than the second electrical potential.

As shown in FIG. 1a, the biasing circuit mentioned above can comprise a dc power source, referenced $V_{13}$, whose positive electrode is connected to the reference voltage $V_{REF}$ and to the third electrode 14, and whose negative electrode is connected to the second electrode 13. Furthermore, this biasing circuit comprises another voltage source, referenced V11, whose positive electrode is connected to the negative electrode of the source $V_{13}$ and whose negative electrode is connected to the first electrode 11.

It can thus be understood that the second electrode 13 forms a cathode electrode, whilst the third electrode 14 forms an anode electrode.

The distance X separating the first, 12, and the second 13 electrode is much greater than the distance D separating the second electrode 13 and the third electrode 14. By way of non-limitative example, for particles charged with high energy and for a frontal inlet of the illumination beam, it is pointed out that for a distance D=100 μm, the distance X can be made equal to 3 mm. However, the small volume of the amplification space 15 makes it possible to choose a distance X, the distance between the first electrode 11 and the second electrode 13, equal to a value very close to the dimension, in this same direction, of the slot Fe in the case of FIG. 1a. Thus the distance X can be made equal to 1 mm in particular in the case in which the gas filling the gas chamber is xenon.

In such a case, when the illumination beam is a beam of X-rays, for example having an energy of 50 keV, then for a photon X there appears in the conversion space 12 a photoelectron of energy 15 keV and a secondary electron, resulting from a radiation of X fluorescence in the gas of energy close to 30 keV, the photoelectron and the secondary electron not being able to be separated in conventional detectors. The appearance of two signals in these detectors results in rejecting the event. The reduction of the distance X to a value of the order of one millimeter has the effect of very greatly reducing the probability of capturing the X fluorescence photon, which therefore makes it possible to eliminate the appearance of a double signal.

Furthermore, and according to a particularly noteworthy aspect of the device which is the subject of the present invention, the voltage sources $V_{13}$ and $V_1$ can be chosen such that the electrical potentials applied to the first, 11, to the second, 12, and to the third electrode make it possible to generate a first, $E_1$, and a second, $E_2$, electrical field, these electrical fields being constituted by parallel electrical field vectors in the conversion space 12 and in the amplification space 13. These electrical fields being perpendicular to the said electrodes and having an amplitude ratio $\rho = E/E_1 > 10$.

In a non-limitative embodiment, it is pointed out that the ratio ρ is made equal to 50.

Furthermore, it is pointed out that the second electrode is formed by a grid pierced with holes and allows the transmission of the electrons generated in the conversion space 12 towards to the amplification space 15 which, taking account of the field amplitude values and of the amplification distance D, makes it possible to ensure the multiplication of these electrons in the amplification space 15 by an avalanche phenomenon confined to the said amplification length D in order to generate multiplied electrons in the vicinity of the third electrode 14 forming an anode.

It is pointed out that, advantageously, the third electrode 14 is formed of elementary anodes under conditions which will be described later in the description.

Finally, a detection circuit 3 is provided, which makes it possible to ensure the detection and counting of the multiplied electrons, this detection and counting circuit 3 being coupled to the elementary anodes forming the anode 14.

In a preferred embodiment, it is pointed out that the voltage sources $V_{13}$ and $V_{11}$ are chosen such that a field $E_2$ is generated, in the amplification space 15, of amplitude 100 kV/cm, for a filling at atmospheric pressure whilst the electrical field $E_1$ generated in the conversion space 12 has an amplitude equal to 1 kV/cm, which makes it possible to obtain a ratio $\rho=100$.

The configuration of the detector element 1 as shown in FIG. 1a, that is to say the values of the said dimensions D and X and the value of the field ratio generated between the amplification space 15 and the conversion space 12, allows a particularly noteworthy functioning in that the electrons created in the gas-filled conversion space 12 are transmitted through the cathode electrode 13 into the amplification space 15 wherein, because of the very high value of the electrical field $E_2$, these electrons are subject to an avalanche phenomenon, which is of course confined to the avalanche distance D, which is very small. For this reason, the avalanche front, that is to say the dimension in a direction perpendicular to the direction of the electrical field $E_2$, is also very small, at most equal to the multiplication distance D/10 for a gain of 1000. In fact, an electron which penetrates into the amplification space 15 is multiplied by successive shocks. For an amplification gain of the order of 1000, where $1000 \# 2^n$, then n=10, and the mean free multiplication path is $\lambda=D/10$.

The size of the avalanche front is therefore of the order of $\lambda$, that is to say D/10. Thus, the real dimension of the avalanche patterns generated by the multiplication of each electron in the amplification space 15 reaches at most, in the vicinity of the electrode 14, a value of the order of that of the free path $\lambda$ of the order to D/10, which makes it possible to achieve a resolution value corresponding to this dimension due to the use of elementary anodes of corresponding size, as will be described hereafter in the description.

Furthermore, it is also pointed out that, because of the proximity due to the low value of the multiplication distance D between the second cathode electrode 13 and the third anode electrode 14, the positive ions created because of the avalanche phenomena, positive ions capable of creating a space charge at the level of the anode 14, are absorbed in a very short time, of the order of 100 ns, which allows a very high counting rate, higher than about $10^6$ strikes/s/mm². The counting rates allowed are therefore between 100 and 1000 times higher than those which are likely to be achieved with the conventional chambers with wires.

On the contrary, it is pointed out that in detectors of the conventional type, such as chambers with wires, the collection time of the positive ions can be as long a several tens of $\mu$s as a consequence of which the counting rates are limited to values 100 times lower.

For a more detailed description of the said detector element 1, it will be possible to refer usefully to the French Patent N° 95 11928 in the name of Georges CHARPAK and of the COMMISSARIAT A L'ENERGIE ATOMIQUE, incorporated as a reference.

Figure 1C:
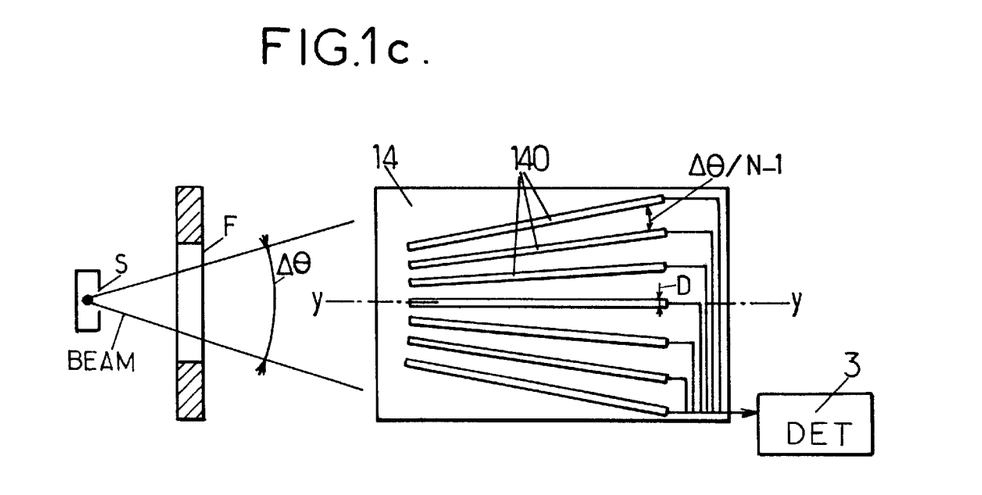
FIGS. 1c and 1d show a cross-sectional view along the transverse cross-section plane AA of FIG. 1a relative to a first and to a second variant embodiment of the high resolution radiographic imaging device which is the subject of the present invention.

In a particularly advantageous way, as shown in FIG. 1c, the elementary anodes constituting the third electrode forming the anode 14 can be formed by electrically conductive elements, referenced 140 in the said FIG. 1c, these elementary conductors having an axis of longitudinal symmetry referenced YY in this figure. As can be seen in the said figure, the axis of longitudinal symmetry YY of each electrically conductive element 140 is oriented such that they converge towards the ionizing radiation source S, the point of emission of the illumination beam. Such an arrangement makes it possible to substantially eliminate the parallax error due to the projection of the plane of the illumination beam on the plane of the third electrode 14 constituting the anode.

In the embodiment shown in FIG. 1c, the electrically conductive elements 140 are formed by electrically conductive strips formed by copper microstrips having a width which can be between 80 and 200 $\mu$m for example and a thickness of a few $\mu$m. These strips can be made by micro-photogravure and covered with a conductive film of gold or copper. They are formed on an insulating substrate such as an epoxy glass material or a sheet of plastic material such as KAPTON for example.

Furthermore, each strip 140 is connected to the detection and counting circuit 3 as will be described in a more detailed manner later on in the description. For an angle of divergence $\Delta\Theta$ of the illumination beam in the plane of the anode electrode 14, each elementary electrode 140 is then spaced from an adjacent elementary electrode by an angle $\Delta\Theta/N-1$ when a number N of electrodes is provided, the elementary electrodes 140 thus being spaced regularly in the angle of divergence of the illumination beam.

Figure 1D:
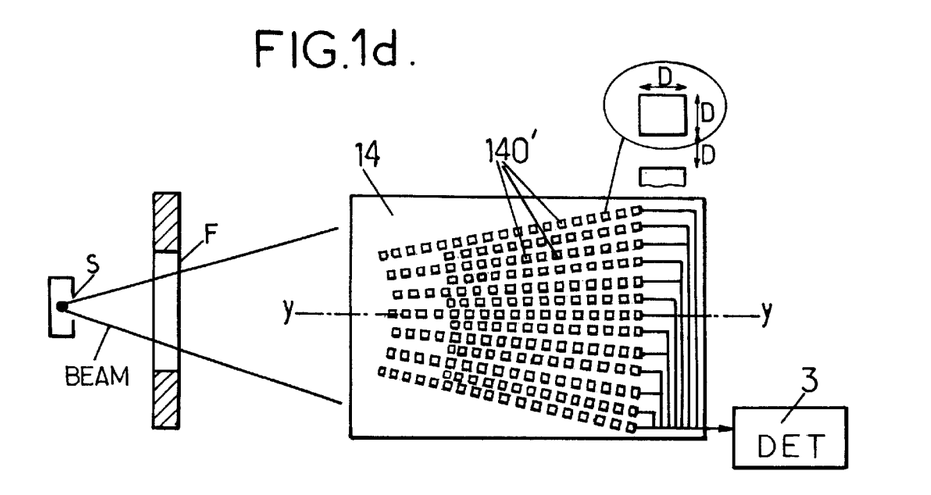

According to a variant embodiment shown in FIG. 1d, it is furthermore pointed out that the electrically conductive elements constituting the elementary anodes 140' may also be constituted by pads distributed along a plurality of longitudinal axes YY, as in the case of FIG. 1c, these electrically conductive element pads each constituting an elementary anode and having a dimension in a direction perpendicular to the direction of the axis of longitudinal symmetry YY substantially equal to the amplification distance. Thus, each elementary anode 140' can have a substantially square shape whose side is equal to or less than the multiplication distance D, two successive elementary anodes being spaced, for example, both in the longitudinal direction YY and in a direction perpendicular to this longitudinal direction, by the same distance D. In the case of FIG. 1d, it is pointed out that the electrically conductive elements forming the elementary anodes 140' are also spaced regularly in the angle of divergence of the illumination beam. Each elementary anode 140' is of course itself interconnected with the detection and counting circuit 3.

The advantage of the said configuration of elementary anodes consists in particular in the fact that, as the avalanche phenomena develop only over the multiplication distance D, it is easy to choose the distribution of these elementary anodes in order to obtain the best precision, whereas in chambers with wires a minimum distance between wires equal to 1 mm is necessary in order to ensure satisfactory functioning.

Figure 2A:
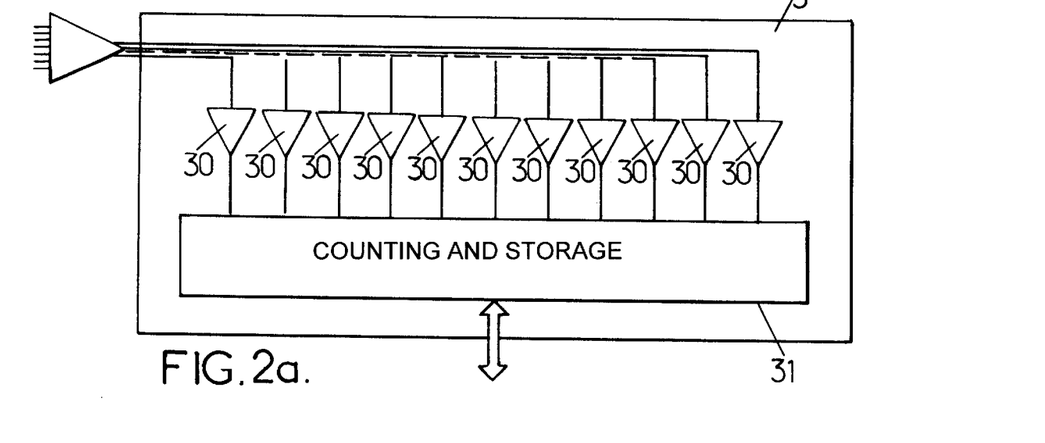
FIG. 2a shows a detail of the embodiment of specific detection circuits used by the high resolution radiographic imaging device according to the invention.

As furthermore shown in FIG. 2a, it is pointed out that the detection and counting circuit 3 can advantageously comprise a plurality of fast amplifiers 30, each fast amplifier 30 of course being interconnected with an elementary anode 140' and supplying a detection signal for the elementary anode in question. Finally, the output of each fast amplifier is, for example, interconnected with a counting and storage circuit 31.

In order to ensure the transmission of electrons generated in the conversion space, the second electrode 13 forming a cathode electrode is advantageously formed by a thin electrically conductive plate. This plate is pierced with holes represented in a non-limitative way by circular holes in FIG. 2b, each hole $130_i$ being distant from another hole by a pitch P and having a dimension T in order to form an array of holes such as shown in the said figure. The thickness e of the plate is small in comparison with the dimension T of the holes. The electrical field in the multiplication space is then chosen to be sufficient for the electrons to pass through the grid.

Figure 2B:
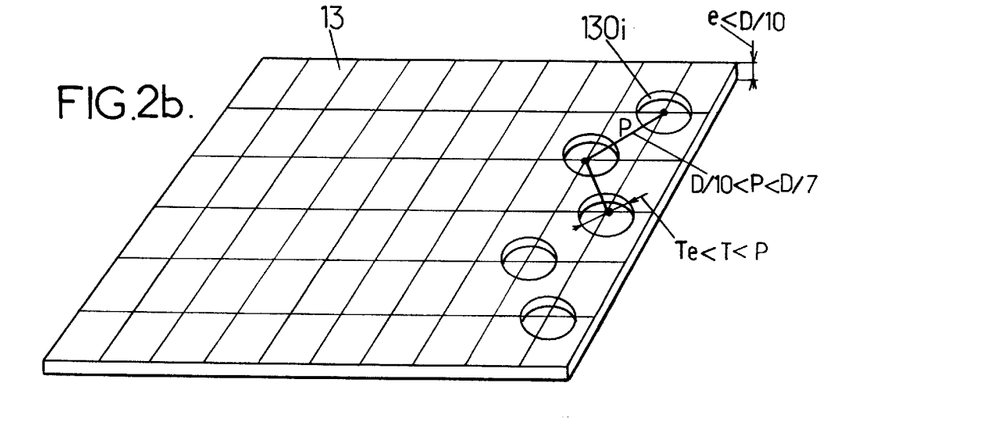
FIG. 2b shows a detail of an advantageous embodiment of the grid forming the cathode of a detection element according to the subject of the present invention.

Advantageously, the pitch P of the array is such that D/10<P<D/3.

Furthermore, the biggest dimension T of each hole $130_i$, this dimension corresponding to the diameter of the holes when the latter are circular, is very much greater than the thickness e, in a ratio of greater than 5 and such that: e<<T≦P. The grid constituting the second electrode 13 forming the cathode can be embodied by an electro-formed a grid whose thickness e can be of the order of 2 to 5 $\mu$m, the diameter of the holes being, for example, equal to 20 $\mu$m and the pitch being equal to 25 $\mu$m.

In a particular embodiment, the plate forming the second electrode 13 comprised a grid of thickness 3 $\mu$m, pierced with 20 $\mu$m square holes, T=20 $\mu$m and spaced by the pitch P=25 $\mu$m.

From the point of view of the mechanical assembly of the second electrode forming the cathode 13 and in order to ensure the mechanical strength of the latter, particularly in the presence of the electrostatic forces applied by the electrical biasing fields, electrically insulating spacers, referenced 150 in FIG. 1a, must, for large areas, be provided in the amplification space 15 in order to allow the holding of the cathode 13 and of the anode 14. The electrically insulating spacers can be formed by quartz wires, for example, whose diameter corresponds to the multiplication distance D.

The high resolution radiographic imaging device which is the subject of the invention, such as described above in the description, makes it possible to carry out high accuracy analyses such as those required for diagnostic applications in mammography.

Figure 3A:
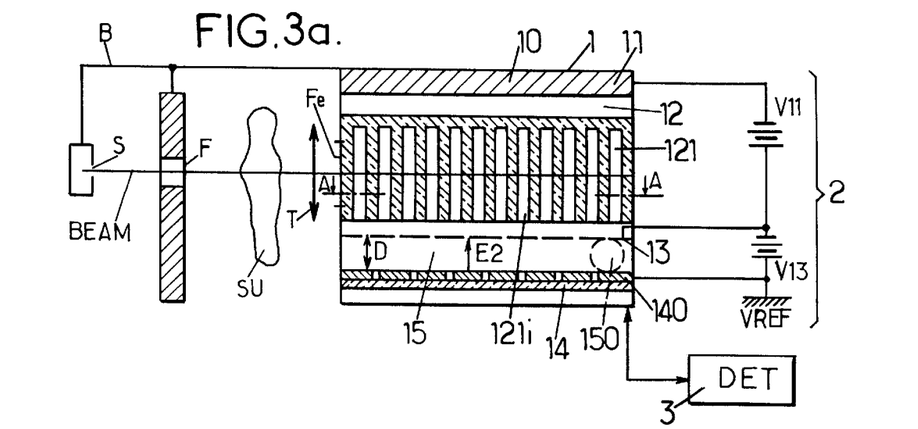
FIGS. 3a and 3b show an advantageous embodiment of a high resolution radiographic imaging device according to the invention, wherein a multi-channel structure is placed in the ionizing radiation conversion space of a detector element used by this device, and a detail of the embodiment of this multi-channel structure.

A more detailed description of a variant embodiment of the high resolution radiographic imaging device which is the subject of the present invention will now be given with reference to FIG. 3a.

In the said figure, it is pointed out that the device which is the subject of the present invention comprises, in the conversion space 12, a multi-channel structure, referenced 121, which allows the capture of the illumination beam and the creation of electrons. In particular it is pointed out that the multi-channel structure 121 is provided with a plurality of channels extending in the direction of the first electrical field E1. The ionizing radiation absorbed by the multi-channel structure thus causes the creation of electrons, which ionize the gas which is in the channels and thus release electrons which are accelerated in the corresponding channels and then transmitted through the second cathode electrode 13 into the amplification space 15.

A neutral particle, such as a gamma ray, can have a very low probability of being absorbed in the conversion space 12 in the absence of a multi-channel structure; the presence of such a structure in this conversion space 12 makes it possible to absorb a much higher number of gamma rays by the Compton or photoelectric effect or by the creations of pairs. The electrons ejected from the surfaces of the channels have a path limited by the thickness of these channels. They ionize the gas which is in the tube and release electrons which penetrate into the amplification space 15 as will be described hereafter.

Figure 3B:
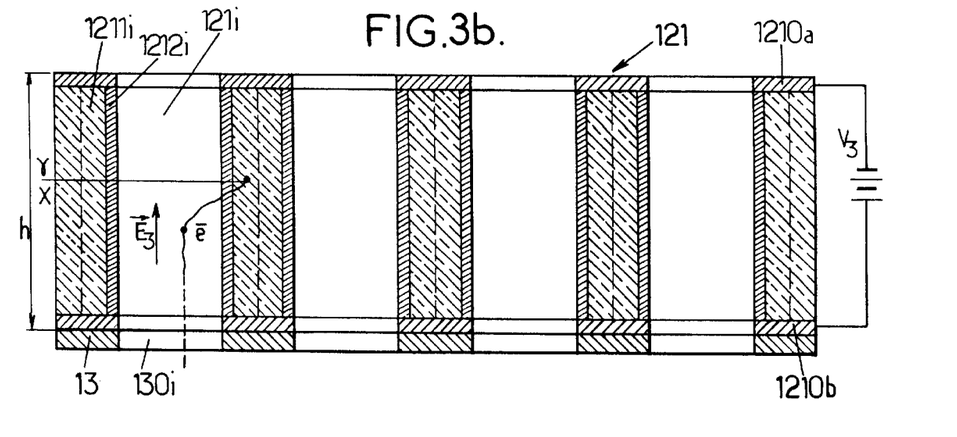

In a preferred embodiment, as shown in FIG. 3b, the structure 121 is a micro-channels structure provided with parallel channels, referenced $121_i$, having at least one opening emerging on a flat surface of this structure.

As furthermore shown in the said FIG. 3b, the assembly of these openings forms, on the flat surface of the micro-channels structure, an array of holes at the same pitch P and with the same dimension T as the array of holes $130_i$ existing on the grid forming the second electrode 13.

In a preferred embodiment, the flat surface of the micro-channels structure having all of the holes of each channel is placed in the vicinity of the second electrode 13 forming the cathode and, of course, in electrical contact with the latter. Thus, an opening of the array of openings of each channel $121_i$ is placed opposite a hole of the grid $130_i$, forming the second electrode 13.

More specifically, it is pointed out that the structure 121 shown in FIG. 3b can be formed by glass tubes placed side by side. These glass tubes can have a thickness of the order of 2 $\mu$m and the walls of the latter bear the reference $1211_i$. The height h of the assembly, that is to say the height of the glass tubes, is of the order of 1 to 2 $\mu$m.

A metal deposit of gold can be produced on the faces of the micro-channels structure, this deposit being referenced 1210a in FIG. 3b. The diameter of each channel $121_i$, taking account of the gold deposit, can be between 10 and 30 $\mu$m.

The micro-channels structure thus produced makes it possible, for holes of diameter 12 $\mu$m and glass tube walls of 2 $\mu$m for example, to form a structure of which 25% of the volume is occupied by the glass. Such a structure has a average density of 0.7 g/cm$^3$ whereas, in the absence of a micro-channels structure, the gas present in the chamber, such as xenon for example, at a pressure of 5 bars, has a density of 0.03 g/cm$^3$.

The introduction of the micro-channels structure 121 thus allows an increase by a factor of 20 in the average density of the material intended to capture the ionizing radiation, and therefore a consequently increased probability of capture.

With tubes having a wall thickness of 2 $\mu$m, the photo-electrons or Compton electrons generated because of the capture have a high probability of escaping the glass walls and of emerging into the holes or channels $121_i$, provided that these photoelectrons have energy higher than a few keV.

According to a particularly advantageous aspect of the micro-channels structure device shown in FIG. 3b, an electrical field $E_3$ can then be created inside each hole, this electrical field being substantially longitudinal and parallel with the axis of each hole $121_i$. For this purpose, the surfaces of each channel $121_i$ can comprise an electrically conductive coating $1212_i$ having high resistivity. This coating is electrically connected to electrodes constituted by the gold coatings $1210_a$ and $1210_b$, each placed on the flat face of the micro-channels structure and a voltage for deflecting electrons in the channels $121_i$ is applied to the electrodes 1210a and 1210b. Each electron emerging into one of the channels $121_i$ is then subjected to a deflection phenomenon because of the existence of the electrical field $E_3$ represented in FIG. 3b. The coatings $1212_i$ of each channel $121_i$ can be formed by a film of lead with a thickness of a few tens of Angstroms. The electrical field E3 can be created by an appropriate voltage source $V_3$. The ionization electrons released into the channels of the micro-channels structure can furthermore be multiplied, prior to their transfer into the amplification space 15, by using the conversion space as one of the multi-stage chambers such as proposed by Monsieur Georges CHARPAK. More specifically, it is pointed out that the said micro-channels structure can be used either with lateral inlet of the illumination beam, as shown in FIGS. 3a and 3b, or with frontal inlet of the illumination beam, as shown in FIG. 3b, in order to detect soft X rays, in particular for the purpose of carrying out crystallographic analysis tasks.

A more detailed description of a particular embodiment of the circuit for the detection and counting of the multiplied electrons allowing a two-dimensional detection, produced in particular by the use of a circuit with coupling by electrical influence with the elementary anodes described previously in the description, will now be given with reference to FIGS. 4a to 4d.

Figure 4A:
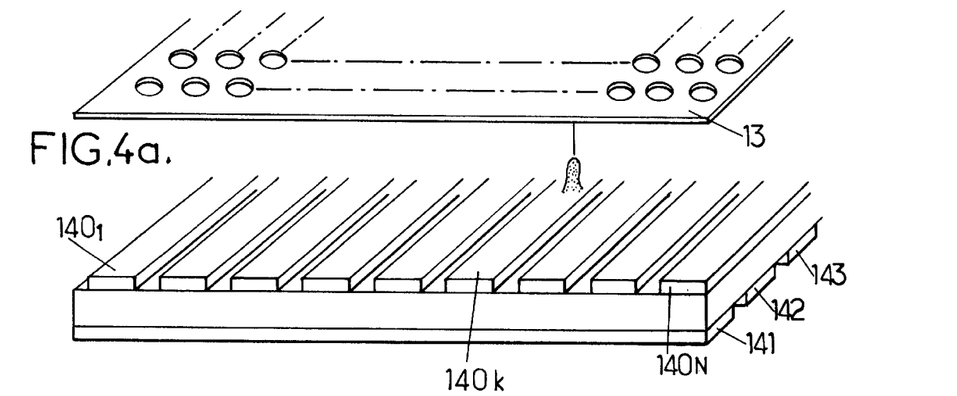
FIGS. 4a to 4d show a variant embodiment of the high resolution radiographic imaging device, which is the subject of the invention, wherein a capacitive coupling circuit is used to ensure the detection of the electrons generated by the ionizing radiation.

As shown in FIG. 4a, the elementary anodes can be constituted by first parallel conductive strips $140_i$, $140_k$, to $140_N$, taken to the same electrical potential $V_{REF}$, as described in above in the description.

Furthermore, a circuit for coupling by electrical influence is formed by second conductive strips 141, 142, 143 and the following ones, these second strips being perpendicular to the first ones, regularly spaced, and giving rise, by an electrical influence phenomenon of charges in motion, to a signal whose sign is opposite to that appearing on the first strips $140_k$.

Taking account of the said coupling by electrical influence, the electrons collected on the conductive strip $140_k$ for example radiate over one or more strips 141, 142, 143 . . . , those located close to the impact of the electrons on the strip $140_k$, the strip 142 for example, a variable electrostatic field which suddenly disappears when these electrons are collected by the conductive strip $140_k$, which allows the production on the strips $140_k$ and 142 of a position pulse of positive sign and a two-dimensional reference X, Y, of the point of impact. The positive ions which are produced on the strips 140k, the elementary anodes, and moving away from the latter, induce negative signals on the latter but the electrostatic field lines radiated over the second strips 141 to 143 and the following ones are firstly positive, which makes it possible to distinguish the pulse types X, Y and therefore allows two-dimensional detection.

By way of non-limitative example, the first and second conductive strips can be formed on a substrate made of insulating material and of appropriate thickness, the dimensioning of the thickness, width and spacing of the strips being determined experimentally.

Figure 4B:
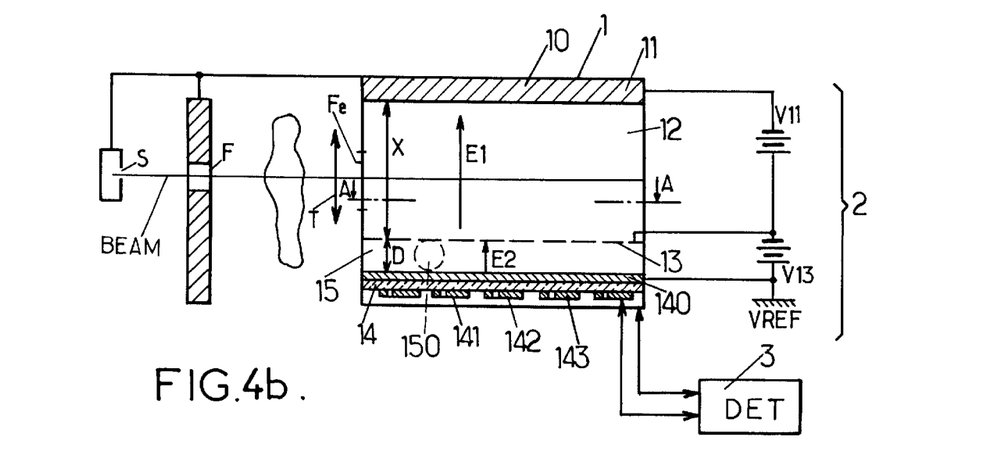

As will be seen in FIG. 4b, it is observed that the second anode electrode 14 can be formed on a board of electrically insulating material, of the printed circuit type, on the upper face of which, opposite the amplification space 15, are placed the elementary electrodes $140_k$ described above in the description.

In the said embodiment, it is pointed out that the detection and counting circuit 3 may furthermore comprise an electrostatic detection circuit, placed in the extension of the strips $140_k$ forming elementary anodes, a variant embodiment of the one shown in FIG. 4a, each reference 1410, 1420, 1430 corresponding for example to an electrically conductive strip. This electrically conductive strip is subdivided according to a periodic pattern into two elementary strips whose electrostatic coupling with each elementary anode $140_k$ are an increasing and decreasing function respectively of the row k of the elementary anode to which each elementary strip 1410, 1420, 1430 is coupled.

Figure 4C:
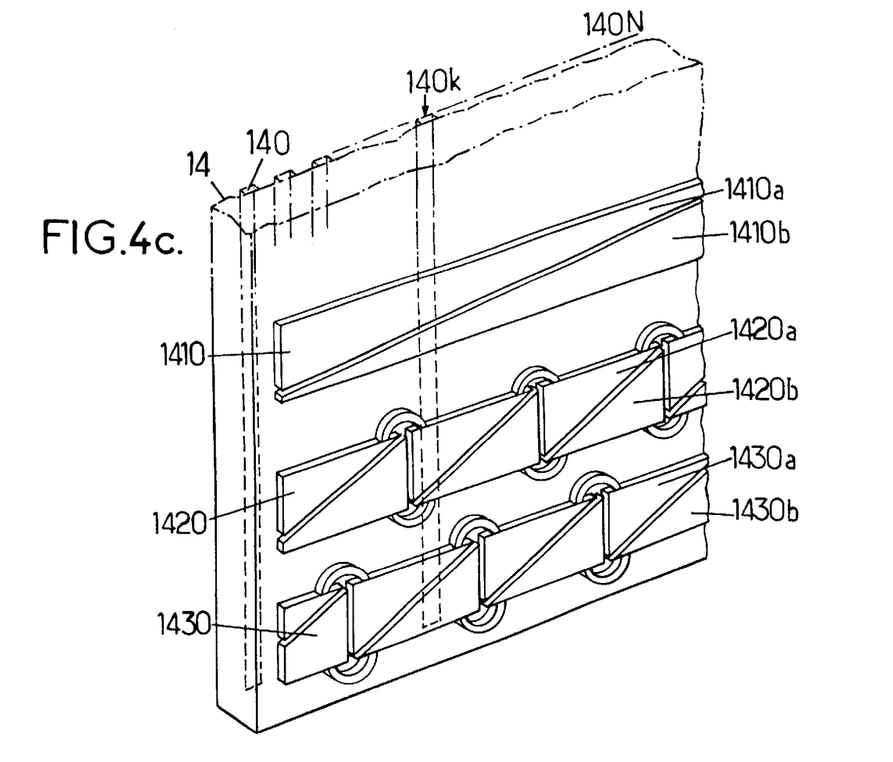

As shown in a more detailed way in FIG. 4c, the elementary strip 1410 for example is subdivided into two elementary strips $1410_a$, $1410_b$, whose electrostatic coupling with each elementary anode $140_k$ are an increasing and a decreasing function respectively of the row of the strip in question.

Figure 4D:
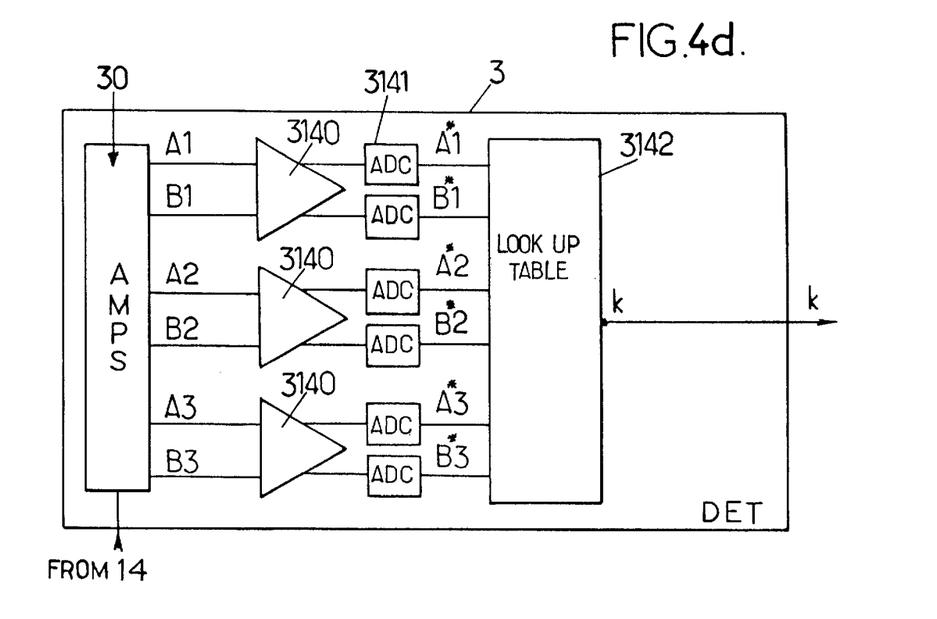

A circuit, such as shown in FIG. 4d, makes it possible to measure the amplitude of the end signal, generated at the end of the first $1410_a$ and of the second $1410_b$ elementary strip, and the ratio of the end signals. This ratio is representative of the row of the elementary anode, row k, in the vicinity of which the ionization electrons have induced the corresponding electrical pulse.

As shown in FIG. 4c, it is pointed out that a second strip 1420 can be provided, this strip also being an electrically conductive strip and subdivided into a first $1420_a$, and a second, $1420_b$, elementary strip according to a same periodical pattern whose periods are multiples of the first electrically conductive strip 1410 in a given ratio.

Furthermore, a third strip 1430 can be provided, which is itself subdivided into elementary strips $1430_a$, $1430_b$. The spatial period of the third strip 1430 is also a multiple of the first electrically conductive strip in another ratio.

The circuit shown in FIG. 4d makes it possible to measure the amplitude of the signals generated by the capacitive coupling at the end of the first 1410 and of the second 1420 elementary strip and the amplitude ratio of these end signals. The first and second electrically conductive strips 1410, 1420, associated if applicable with the third electrically conductive strip 1430 which is itself subdivided into two elementary strips $1430_a$, $1430_b$, thus form a measuring system of the vernier type, of the row k of each elementary anode $140_k$ located substantially opposite the firstly emitted ionization electrons. In FIG. 4d, the circuit 3 for detecting and counting is considered to comprise a logic circuit of the controlled switch type, the circuits 3140 representing amplifier circuits, the circuits 3141 representing analog to-digital converters and the circuit 3142 representing a conversion table making it possible to supply the row k of each elementary anode 140k on which the pulse was detected.

For a more detailed description of the functioning of the electrostatic detection system shown in FIGS. 4c and 4d, it will be possible to refer to the French patent application N° 2 680 010 in the name of Monsieur Georges CHARPAK.

Finally, it is indicated that a set of electrodes 1410, 1430 forming a capacitive detection circuit, for a one-dimensional detection of the elementary anodes $140_k$, can be provided in order to produce, in the same way, a capacitive detection circuit for a one-dimensional detection of the second elementary strips, 140, 141, 142 . . . and the following ones, in the second direction. This set of electrodes is then placed on an extension of the elementary strips 140, 141, 142 and the following ones, as in the case of the elementary anodes $140_k$.

For the use of devices, such as shown in FIGS. 1a, 1b to 4d described above in the description, it is pointed out that the gas contained in the gas chamber can be xenon mixed with a "quenching" agent such as $CO_2$ or ethane at a pressure between $10^2$ and to $10^6$ Pa or, if necessary, a mixture of argon and methane in a volumetric ratio of 90% argon and 10% methane.

However, the gas contained in the gas chamber 10 can be constituted by a mixture of argon and triethylamine, in order to make it possible to cause, in the amplification space 15, a multiplication of the electrons by the luminous avalanches phenomenon.

Figure 5A:
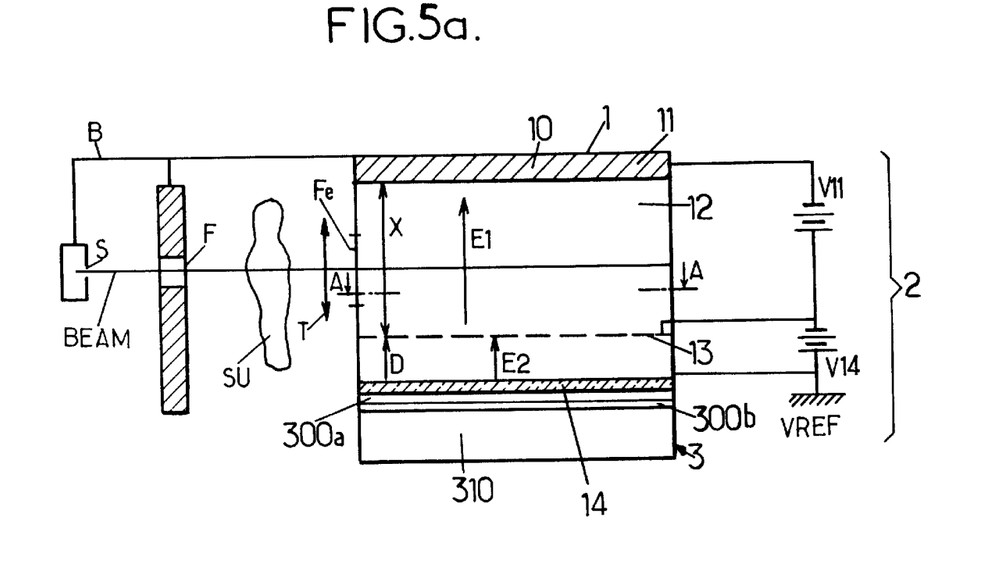
FIGS. 5a and 5b show another variant embodiment of the high resolution radiographic imaging device, which is the subject of the invention, wherein the detection of the electrons generated by the ionizing radiation is carried out by means of the creation of luminous avalanche phenomena.

In such a case, as shown in FIG. 5a, the elementary anodes are formed by transparent electrically conductive elements allowing the transmission of the light generated by the luminous avalanches thus created.

In the embodiment described with reference to FIG. 5a, the detection and counting circuits 3 are for example constituted by a brilliance amplifier $330_b$, equipped with appropriate optics $300_a$, followed by an integrator system 310, such as a photosensitive film or a CCD camera system for example. The CCD camera brilliance amplifier assembly $300_a$, $300_b$, 310 is then placed on the surface of the electrode making it possible to transmit or change the wavelength of luminous avalanches phenomenon thus generated, 280 nm in the case of triethylamine in the visible light range.

Figure 5B:
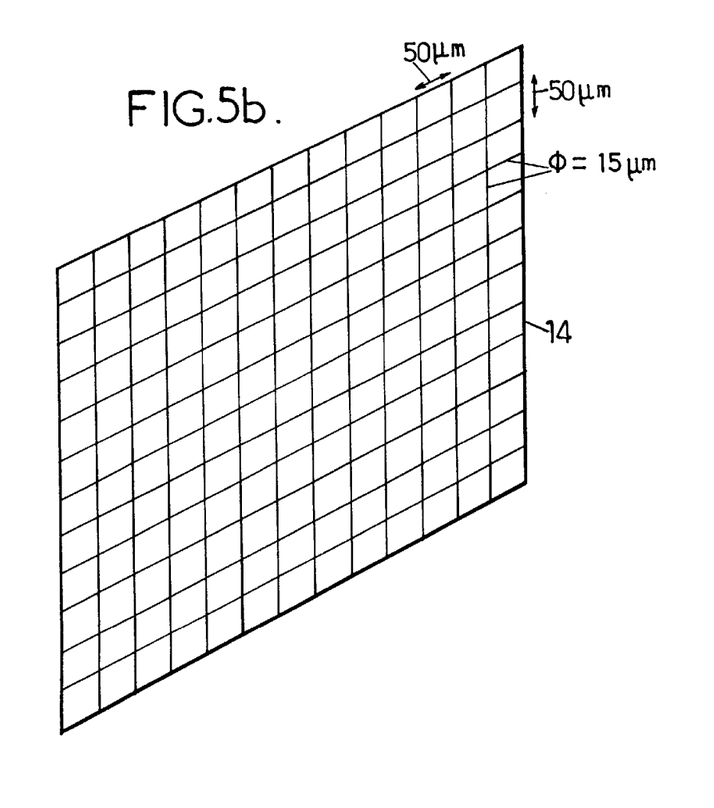

By way of non-limitative example, as shown in FIG. 5b, it is pointed out that the elementary anodes can be formed by an electrically conductive grid associated with a surface allowing either the transmission of the light at the wavelength of the luminous avalanche phenomenon, or the changing of the wavelength of the luminous avalanche phenomenon into a wavelength in the visible range spectrum. By way of non-limitative example, the electrically conductive grid such as shown in FIG. 5b can be formed by conductive wires, gold-plated tungsten wires of diameter 15 $\mu$m with a rectangular pitch of 50 $\mu$m×50 $\mu$m. Each elementary transparent 50 $\mu$m zone in fact constitutes the equivalent of an elementary anode through which the luminous energy of the luminous avalanche created is transmitted. This grid can also be constituted by a grid similar to the second electrode 13 shown FIG. 2b. The said grid can then be placed against a UV/visible light converter. The grid as shown in FIG. 5b is of course taken to the reference potential $V_{REF}$ and thus constitutes the anode constituted by an assembly of transparent elementary anodes. The gas chamber is then closed by the intermediary of a quartz window or of a window made of plastic material for example.

The advantage of the embodiment shown in FIG. 5a wherein a detection of luminous avalanches phenomena is carried out, in comparison with devices of the prior art similarly providing detection of luminous avalanches, is in the fact that as the fronts of the avalanches are much narrower, a greater accuracy is obtained with respect to their position as well as better brilliance.

This improvement appears to be very important when the detection is not made strike by strike by means of electronic circuits, but by means of an integration of luminous photons. Such an operating method is especially important when the emission source S delivers a very intense burst of X or γ rays, an emission source such as a linear accelerator used in radiotherapy. In such a case, it can be necessary to display simultaneously hundreds of thousands or millions of avalanches, which cannot be achieved with conventional electronic means. It is then possible to use, as a particles/ionizing electrons converter, a micro-channels structure, such as described above in the description, or a lead-bismuth matrix such as described in the article published by A. P. JEAVONS, G. CHARPAK and R. J. STUBBS, Nuclear Instruments and Methods 124 (1975), 491–503, North-Holland Publishing and Co. An efficiency of 10 to 50% for gamma rays of 6 MeV currently used in radiotherapy can be obtained with an image accuracy of 0.5 mm to 1 mm. It is thus possible to produce a radiograph of the patient, whilst the latter is being treated and subjecting him to a radiation dose very much lower than that of the treatment. Thus, luminous detection constitutes a means of obtaining high accuracy, in particular when appropriate optics $300_a$, a brilliance amplifier $300_b$ and a CCD camera for example, 310, are used. In this application, the illumination beam can be inlet either laterally, in accordance with the method shown in FIG. 1a, or frontally, as shown in FIG. 1b.

In the case of lateral inlet of the illumination beam, a measurement can be taken every 50 ms, that is one frame duration of the CCD camera used, whilst one displacement of the detection module is carried out.

However, a frontal inlet appears particularly appropriate when the detection module comprises, in the conversion space 12, a micro-channels converter and the image is acquired of all of the avalanches generated by a pulse or "flash" of γ rays, such as used in radiotherapy by means of a linear accelerator emitting γ rays for very short periods. In such an application, as the luminous avalanches are very narrow, a good image resolution is obtained directly without any need to carry out image processing such as calculation of the centroid, the optical centre of gravity, of each avalanche, as previously proposed by Monsieur Georges CHARPAK. This operating method therefore makes it possible to obtain a great saving in equipment and calculating time in comparison with the devices of the prior art.

In addition to the said applications in X or gamma radiography, the device which is the subject of the present invention can be used to great advantage in β radiography, in specific conditions which will be described hereafter, with reference to FIG. 5c. As shown in the said figure, in this application, the ionizing radiation source consists in this case of an electrophoresis gel, a section or a preparation, bearing the reference G, the gel, the section or the preparation being radioactively marked in the conventional way. The electrophoresis gel G is then the site of points of emission of β rays distributed over the cross-section of the gel, the section or the preparation, the illumination beam then consisting of a plurality of β beams emitted sporadically at these various emission points. The gel G is placed in the vicinity of the window Fe for a frontal inlet of the illumination beam. A support SUP, represented by dotted and dashed line in FIG. 5c makes it possible, if necessary, to position the gel, the section or the preparation for observation.

According to a specific characteristic of the detector which is the subject of the present invention, that latter is such that the first electrode 11 and the second electrode 13 are distant by a distance X close to or less than that of the distance D separating the second electrode 13 from the third electrode 14. The conversion space 12 and the amplification space 15 thus have a substantially equal dimension in the direction perpendicular to the electrodes 11, 13 and 14.

By way of non-limitative example, for a distance D=100 $\mu$m, the distance X can be made equal to this value X=100 $\mu$m. The total thickness of the detector 1 is then 0.2 mm.

Figure 5C:
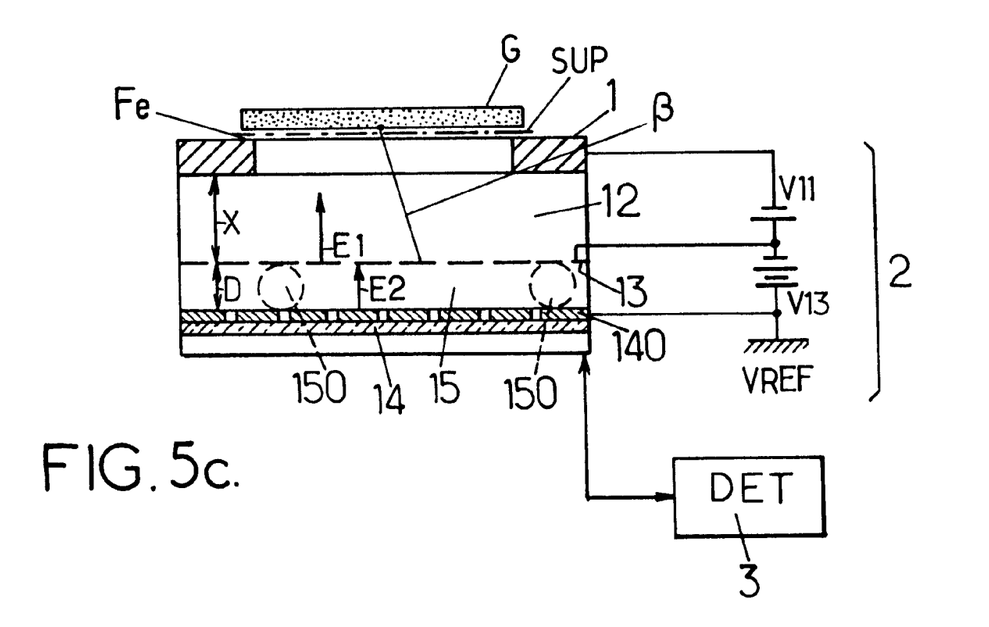
FIG. 5c shows a high resolution radiographic imaging device according to the subject of the present invention using β imaging.

In these conditions, a β ray emitted from any emission point in the gel G has, as shown in FIG. 5c, a maximum path of the order of magnitude of the distance X separating the first and the second electrodes 11,13. As the electrons are generated in the conversion space 12, on the path of the β ray, the accuracy of location of the corresponding emission point is better than the value of this distance X. The detector device which is the subject of the present invention makes it possible to develop devices which are simpler than the present devices having chambers with parallel faces in which the location of the point of emission of the β ray is carried out by means of the variable gain according to the depth of the ionization electron along the z coordinate.

A more detailed description of a high resolution radiographic imaging device using X or γ ionizing radiation making it possible to carry out analyses of three-dimensional images in a single exposure will now be given with reference to FIGS. 6a and 6b.

Figure 6A:
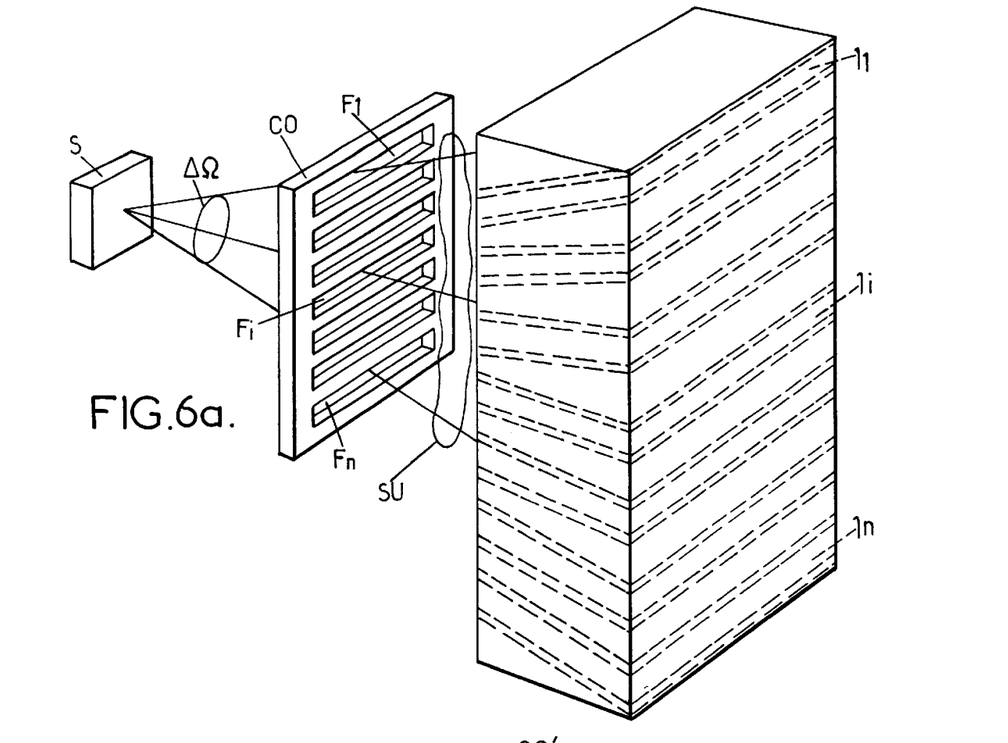
FIGS. 6a and 6b show a high resolution radiographic imaging device according to the subject of the present invention, wherein a plurality of elementary detector elements are arranged by superimposition, in such a way as to allow a three-dimensional analysis of a given subject for an illumination beam having a predetermined solid angle.

According to the said FIG. 6a, the radiation source used S is considered to generate an ionizing radiation beam in the form of a divergent beam having a given solid angle Δω.

According to the embodiment shown in FIG. 6a, the radiographic imaging device according to the invention comprises a collimator CO comprising a plurality of longitudinal slots, referenced $F_1 \ldots F_i, \ldots F_n$, forming a plurality of diaphragms in fact making it possible to deliver a plurality of flat illumination beams as shown in the said figure. Each flat illumination beam is distributed substantially in a plane containing one of the longitudinal slots of the assembly of these slots and the source S. As shown in FIG. 6a, the planes containing one of the flat illumination beams together form a beam of planes converging towards the ionizing radiation source.

As also shown in the said figure, the device according to the invention comprises a module for detecting the set of flat illumination beams, which have made it possible to illuminate the subject to be observed SU, this subject being placed downstream of the collimator CO. This detection module comprises a detector of ionizing particles such as previously described in the description with reference to FIGS. 1a to 5b, this detector 1 being placed facing a corresponding flat illumination beam. In this way, each detector, referenced $1_1$, $1_i$ to $1_n$, corresponds to a slot $F_1$, $F_i$ to $F_n$, and in particular, the window $Fe_1$, $Fe_1$ to $Fe_n$ of each of these detectors, being the window for the inlet of the flat illumination beam, is placed in the plane formed by the ionizing radiation source S and the slot Fi delivering that flat illumination beam with which this detector is associated. The windows $Fe_i$ can be formed, as shown in FIG. 6b in a common collimator CO'.

Figure 6B:
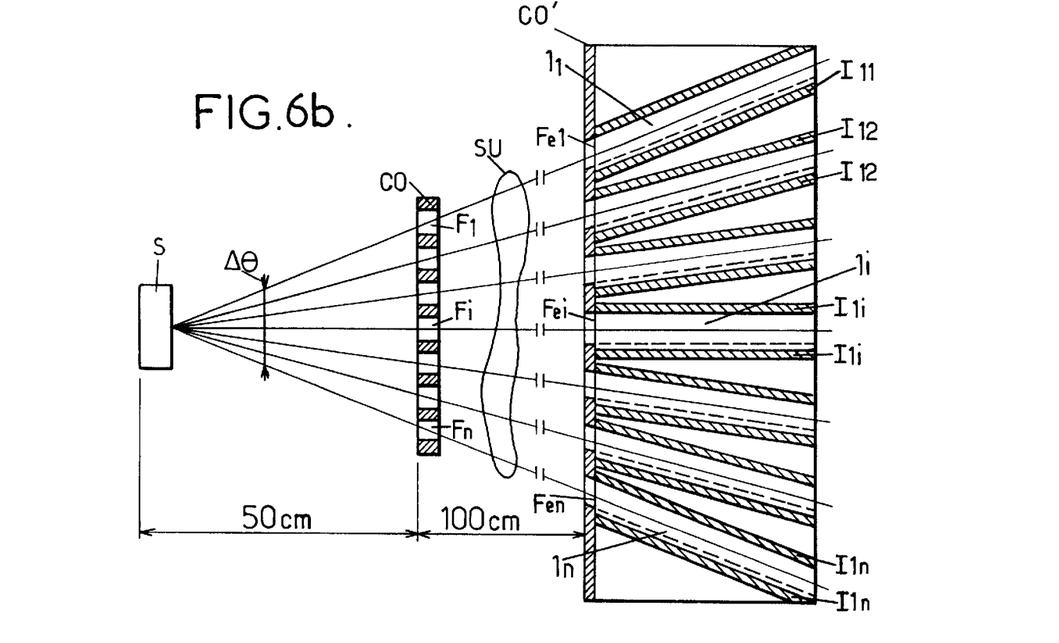

In FIGS. 6a and 6b, it can be observed that the assembly of detectors $1_1$ to $1_n$ is inclined symmetrically with respect to a central detector referenced $1_i$ in the said figures.

In order to ensure the independence of each detector $1_i$, these detectors can be provided with protections, referenced $1_{1i}$, these protections being constituted by a sheet of lead or tungsten making it possible to ensure the independence of each of the detectors $1_i$ with respect to the ionizing radiations diffused by each adjacent flat illumination beam.

There has thus been described a high resolution radiographic imaging device which has a particularly good performance insofar as the detector 1 used has a very small thickness. In fact, taking account of the conversion space 12 and of the amplification space 15, the total thickness is of the order of 1.1 mm. In particular, this specific characteristic of the high resolution radiographic imaging device which is the subject of the present invention makes it possible to use a device comprising multiple detectors such as shown in FIGS. 6a and 6b. These detectors operate as if they were in parallel and the multiplication of detectors, when a number n of detectors is used, makes it possible to save scanning time of the subject SU, in a corresponding ratio n.

It is of course understood that all of the n detectors can be placed in a single pressurized gas chamber with lead separating screens, the screens $1_{1i}$ being those mentioned above in the description, the latter preventing any secondary radiation produced in a detector from disturbing detection in the adjacent detectors.

Finally, in the case in which the ionizing radiation is a high energy radiation such as a γ radiation having energy grater than 1 MeV, appropriate for use in industrial radiography, the detectors 1 used can comprise, instead and in place of the micro-channels structure 12, mentioned above in the description, a plurality of thin inclined sheets, such as tantalum sheets placed at a grazing angle of incidence, of the order to 1°, with respect to the average direction of the illumination flux of ionizing particles, according to a known technique of the prior art. These sheets make it possible to ensure the conversion of the particles.

This embodiment makes it possible, on the one hand, to increase the probability of capture of the ionizing particles and of ejection of the photo-electrons thus generated, in accordance with the technique of the said prior art but, on the other hand, thanks to the use of the very high counting rate capability of the detectors 1 according to the subject of the present invention, to reduce considerably the operating costs of the particle accelerator generating the ionizing particles used.

I claim:
1. A high resolution radiographic imaging device using ionizing radiation comprising a source of ionizing radiation in the form of a divergent beam, a longitudinal slot forming a diaphragm adapted to deliver a flat illumination beam, substantially distributed in a plane containing the longitudinal slot, and means for detecting a beam transmitted through a subject to be observed, illuminated by the flat illumination beam, wherein said detecting means comprise at least one ionizing particles detector comprising at least:

one gas chamber provided with an inlet window for said illumination beam, and in this gas chamber, a first, a second and a third flat electrode, each flat electrode being placed parallel with one another in order to form a conversion space for the conversion of the illumination beam into electrons and an amplification space for the amplification by multiplication of these electrons, said inlet window being placed at the level of the conversion space in order to ensure the inlet of said illumination beam into said conversion space, said amplification space having an amplification length which is formed by the distance separating said second and said third electrodes, of less than 200 μm, said detector furthermore comprising:

biasing means adapted to raise said first electrode to a first electrical potential, said second electrode to a second electrical potential higher than said first electrical potential, and said third electrode to a third electrical potential higher than said second electrical potential, said second electrode being pierced with holes and forming a cathode allowing the transmission of the electrons generated in said conversion space towards the amplification space, and said third electrode forming an anode constituted by a plurality of electrically isolated elementary anodes, said elementary anodes each consisting of pads distributed along a plurality of longitudinal symmetry axes, said pads having a dimension in a direction perpendicular to the direction of longitudinal symmetry substantially equal to the amplification length, the electrical potentials applied to the first, to the second and to the third electrodes allowing the generation of a first and a substantially parallel second electrical field in the conversion space and in the amplification space, each of these electrical fields being substantially perpendicular to the said electrodes with an amplitude ratio greater than 10, thereby allowing the multiplication of these electrons in the amplification space by an avalanche phenomenon confined to said amplification length in order to generate multiplied electrons in the vicinity of said third electrode forming an anode, means for detecting and counting the multiplied electrons which are coupled to said elementary anodes forming said anode.

2. The device according to claim 1, wherein said inlet window is placed, either laterally on the gas chamber in order to allow the inlet of the said illumination beam parallel with said electrodes, or on the face of the gas chamber located opposite the second electrode forming the cathode electrode in such a way as to allow frontal inlet of the said illumination beam with respect to said electrodes.

3. The device according to claim 1, wherein said elementary anodes are formed by electrically conductive elements, said axis of longitudinal symmetry of each electrically conductive element being oriented such that they converge towards the ionizing radiation source which forms the point of emission of said illumination beam, thereby allowing to substantially eliminate the parallax error due to the projection of the plane of the illumination beam on the plane of the third electrode constituting said anode.

4. The device according to claim 3, wherein two consecutive electrically conductive elements along the perpendicular direction are spaced regularly within the angle of divergence of the illumination beam.

5. The device according to claim 1, wherein said means of detection and counting comprise:
   a plurality of fast amplifiers, one fast amplifier being coupled to an electrically conductive element forming an elementary anode, and delivering an electrical detection signal for the elementary anode in question;
   means of counting and storing interconnected at the output of the fast amplifiers.

6. The device according to claim 1, wherein said second electrode is formed by an electrically conductive grid, said grid comprising a regular array of holes whose pitch, P, in the plane of the second electrode is between D/10, D/3, the biggest dimension of the holes T being greater than the thickness e of this grid but less than P.

7. The device according to claim 1 further comprising, in said conversion space, a multi-channel structure allowing the capture of the illumination beam and the creation of electrons, each channel in said multi-channel structure extending in the direction of said first electrical field.

8. The device according to claim 7, wherein said multi-channel structure is a micro-channels structure formed by a block of material absorbing the ionizing radiation of said illumination beam, said structure being provided with parallel micro-channels having at least one opening emerging on a flat surface of this structure, the assembly of these openings forming on this flat surface an array of holes at a same pitch P and with a same dimension T as a array of holes in a grid forming said second electrode, said flat face and said array of openings being placed in the vicinity of said second electrode forming said cathode, an opening of this array of openings being placed opposite a hole of the grid forming said second electrode, the openings and the holes being thus facing one another.

9. The device according to claim 1, wherein said means of detecting and counting furthermore comprise an electrostatic detection circuit consisting of a capacitive coupling with each elementary anode, said electrostatic detection circuit comprising at least a first electrically conductive strip, said electrically conductive strip being subdivided according to a periodic pattern into two elementary strips whose electrostatic coupling with each elementary anode are an increasing and decreasing function respectively of the row k of the elementary anode to which each elementary strip is coupled.

10. The device according to claim 1, wherein the gas contained in said gas chamber is xenon mixed with a "quenching" means at a pressure between $10^2$ and $10^6$ Pa.

11. The device according to claim 1, wherein said gas contained in the gas chamber is constituted by a mixture of argon and trimethylamine, so as to allow to cause, in said amplification space, a multiplication of the electrons by the luminous avalanches phenomenon, said elementary anodes being formed by transparent electrically conductive elements, allowing the transmission of the light generated by the luminous avalanches thus created.

12. The device according to claim 11, wherein said elementary anodes are formed by an electrically conductive grid associated with a surface allowing either the transmission of the light at the wavelength of the luminous avalanche phenomenon, or the changing of the wavelength of the luminous avalanche phenomenon into a wavelength in the visible range spectrum.

13. The device according to claim 12, wherein said means of counting are constituted by integrating means, such as a sensitive film, associated with optical and brilliance amplifier means, placed on the surface allowing the transmission or the change in wavelength of the luminous avalanche phenomenon.

14. A high resolution radiographic imaging device using ionizing radiation, comprising a source of ionizing radiation in the form of a divergent beam, said device including:
   a collimator comprising a plurality of longitudinal slots forming a plurality of diaphragms adapted to deliver a plurality of flat illumination beams, each one distributed substantially in a plane containing one of the longitudinal slots of this plurality of longitudinal slots, the planes containing one of the flat illumination beams together forming a beam of planes converging towards said ionizing radiation source, and
   means for detecting the set of flat illumination beams, said means of detection including at least one detector of ionizing particles comprising at least:
      one gas chamber provided with an inlet window for said illumination beam, and in this gas chamber,
      a first, a second and a third flat electrode, each flat electrode being placed parallel with one another in order to form a conversion space for the conversion of the illumination beam into electrons and an amplification space for the amplification by multiplication of these electrons, said inlet window being placed at the level of the conversion space in order to ensure the inlet of said illumination beam into said conversion space, said amplification space having a multiplication length which is formed by the distance separating said second and said third electrodes, of less than 200 μm,
   said detector furthermore comprising:
      biasing means adapted to raise said first electrode to a first electrical potential, said second electrode to a second electrical potential higher than said first electrical potential, and said third electrode to a third electrical potential higher than said second electrical potential, said second electrode being pierced with holes and forming a cathode allowing the transmission of the electrons generated in said conversion space towards the amplification space, and said third electrode forming an anode constituted by a plurality of electrically isolated elementary anodes, said elementary anodes each consisting of pads distributed along a plurality of longitudinal symmetry axes, said pads having a dimension in a direction perpendicular to the direction of longitudinal symmetry substantially equal to the amplification length, the electrical potentials applied to the first, to the second and to the third electrodes allowing the generation of a first and a substantially parallel second electrical field in the conversion space and in the amplification space, each of these electrical fields being substantially perpendicular to the said electrodes with an amplitude ratio greater than 10, thereby allowing the multiplication of these electrons in the amplification space by an avalanche phenomenon confined to said amplification length in order to generate multiplied electrons in the vicinity of said third electrode forming an anode, means for detecting and counting the multiplied electrons which are coupled to said elementary anodes forming said anode, said at least one detector of ionizing particles being placed facing each flat illumination beam, each detector being placed in the plane formed by the ionizing radiation source and the slot delivering the flat illumination beam with which this detector is associated.

15. The device according to claim 1, wherein for imaging using β radiography, the ionizing radiation source consisting of an electrophoresis gel or a radioactively marked section which is the site of β ray emission points and placed in the vicinity of the window for a frontal inlet of the illumination beam, said first and second electrodes are distant by a distance X close to or less than the distance separating said second and said third electrodes, said conversion space and said amplification space having a dimension substantially equal in a direction perpendicular to the said electrodes, thereby allowing to limit the length of the path of each β ray emitted by the source to a value substantially equal to that of the distance X separating the first and the second electrodes and to bring an accuracy of location of the β ray emission points to a value close to or less than this distance X.

* * * * *